United States Patent [19]
Gray et al.

[11] Patent Number: 5,474,997
[45] Date of Patent: Dec. 12, 1995

[54] METHODS AND COMPOSITIONS OF (2R,4S) ITRACONAZOLE FOR TREATING FUNGAL YEAST AND DERMATOPHYTE INFECTIONS

[75] Inventors: Nancy M. Gray, Marlborough, Mass.; Raymond L. Woosley, Washington, D.C.

[73] Assignees: Sepracor, Inc., Marlborough, Mass.; Georgetown University, Washington, D.C.

[21] Appl. No.: 341,266

[22] Filed: Nov. 17, 1994

Related U.S. Application Data

[63] Continuation of Ser. No. 9,706, Jan. 27, 1993, abandoned.
[51] Int. Cl.$^6$ .................... A61K 31/495; A61K 31/50
[52] U.S. Cl. ............................................................ 514/252
[58] Field of Search .......................................... 514/252

[56] References Cited

U.S. PATENT DOCUMENTS

| | | | |
|---|---|---|---|
| 4,267,179 | 11/1981 | Heeres et al. | 424/25 D |
| 4,490,530 | 12/1984 | Heeres et al. | 544/370 |

FOREIGN PATENT DOCUMENTS

| | | |
|---|---|---|
| WO90/11754 | 1/1990 | WIPO. |
| WO93/19061 | 3/1993 | WIPO. |

OTHER PUBLICATIONS

"Pharmacokinetics of Itraconazole following Oral Administration to Normal Volunteers," by T. Hardin, J. Graybill, R. Fetchick, R. Woestenborghs, M. Rinaldi and J. Kuhn; Antimicrobial Agents and Chemotherapy, vol. 32, No. 9, (1988), pp. 1310–1313.

"In vitro Antifungal Spectrum of Itraconazole and Treatment of Systemic Mycoses with Old and New Antimycotic Agents," by J. Van Cutsem; Journal of Chemotheraphy, vol. 38, Supplement 1, (1992), pp. 3–11.

"Activity of Orally, Topically, and Parenterally Administered Itraconazole in the Treatment of Superficial and Deep Mycoses: Animal Modes," by J. Van Cutsem, F. Van Gerven and P. A. J. Janssen; Reviews of Infectious Diseases, vol. 9, Supplement 1, (1987), pp. S15–S32.

"Antimycotic Azoles. 7. Synthesis and Antifungal Properties of a Series of Novel Triazol-3-ones," by J. Heeres, L. J. J. Backx and J. Van Cutsem; Journal of Medical Chemistry, vol. 27, No. 7, (1984), pp. 894–900.

*Primary Examiner*—Jerome D. Goldberg
*Attorney, Agent, or Firm*—Heslin & Rothenberg

[57] ABSTRACT

Methods and compositions are disclosed utilizing the optically pure (2R,4S) isomer of itraconazole. This compound is a potent drug for the treatment of local and systemic fungal, yeast, and dermatophyte infections, while avoiding the concomitant liability of adverse effects associated with the racemic mixture of itraconazole.

15 Claims, No Drawings

METHODS AND COMPOSITIONS OF (2R,4S) ITRACONAZOLE FOR TREATING FUNGAL YEAST AND DERMATOPHYTE INFECTIONS

This application is a continuation of application Ser. No. 08/009,706, filed Jan. 27, 1993, now abandoned.

BACKGROUND OF THE INVENTION

This invention relates to novel compositions of matter containing (2R,4S) itraconazole substantially free of its (2S,4R) isomer. These compositions possess potent activity in treating local and systemic fungal, yeast and dermatophyte infections while avoiding adverse effects associated with the administration of the racemic mixture of itraconazole. Adverse effects include, but are not limited to, hepatotoxicity, arrhythmia, nausea, vomiting and hypersensitivity reactions, including urticaria, abdominal pain, headache, dizziness, and elevations in serum liver enzymes. Also disclosed are methods for treating the foregoing infections in a human while avoiding the adverse effects that are associated with the racemic mixture of itraconazole by administering the (2R,4S) isomer of itraconazole to said human.

The active compound of these compositions and methods is a specific subset of optical isomers of itraconazole, which is described by Van Cutsem, *Chemotherapy* 38 *Suppl.* 1, 3–11 (1992) and Heeres et al., *J. Med. Chem.* 27, 894–900 (1984). It is generically claimed in U.S. Pat. No. 4,267,179, but it does not appear to be specifically disclosed therein.

Itraconazole is defined in the *USAN and USP Dictionary of Drug Names* as 4-[ 4-[ 4-[ 4- [[ 2-(2,4-dichlorophenyl)-2-(1H-1,2,4-triazol-1-ylmethyl)-1,3-dioxolan- 4-yl] methoxy] phenyl] -1-piperazinyl] phenyl]- 2,4-dihydro-2-(1-methylpropyl)-3H-1,2,4-triazol-3-one or alternatively as (±)-1-sec-butyl-4-[p-[4-[p-[ [(2R*,4S*)-2-(2,4-dichlorophenyl)-2-(1H-1,2,4-triazol- 1-ylmethyl)-1,3-dioxolan-4-yl] methoxy] phenyl]-1-piperazinyl]phenyl]-Δ²-1,2,4-triazolin- 5-one. The commercially available material is the cis isomer in the dioxolane ring and is represented by the structural formula I:

formula I: two in the dioxolane ring and one in the sec-butyl side chain on the triazolone.

The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wedge outlines and dotted or broken lines denote enantiomerically pure compounds of indeterminate absolute configuration; wavy lines indicate disavowal of any stereochemical implication which the bond it represents could generate; and solid and broken bold lines, as in I, are geometric descriptors indicating the relative configuration shown but specifically denoting racemic character.

There are eight possible isomers of a structure having three asymmetric carbons: (R,R,R), (R,R,S), (R,S,S), (S,S,S), (R,S,R), (S,R,S), (S,R,R) and (S,S,R). Because the commercially available itraconazole is a cis isomer, it comprises a mixture of only those isomers that describe a cis relationship in the dioxolane ring. Adopting the convention that the first denoted chiral center is at C-2 of the dioxolane ring, the second is at C-4 of the dioxolane and the third is in the sec-butyl group, commercial itraconazole is a mixture of (R,S,S), (R,S,R), (S,R,S) and (S,R,R) isomers. Compounds of this invention have the (2R,4S) configuration in the dioxolane rings and will henceforth be referred to as (2R,4S) itraconazole. (2R,4S) Itraconazole may comprise a mixture of two diastereomers: (R,S,S) (II) and (R,S,R) (III).

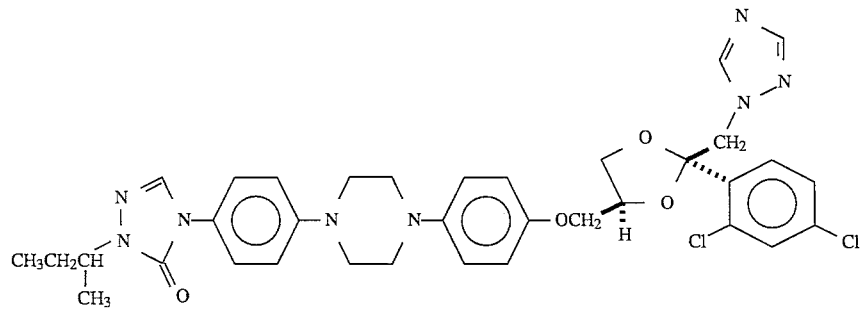

I

It will be noted that there are three asymmetric carbons in

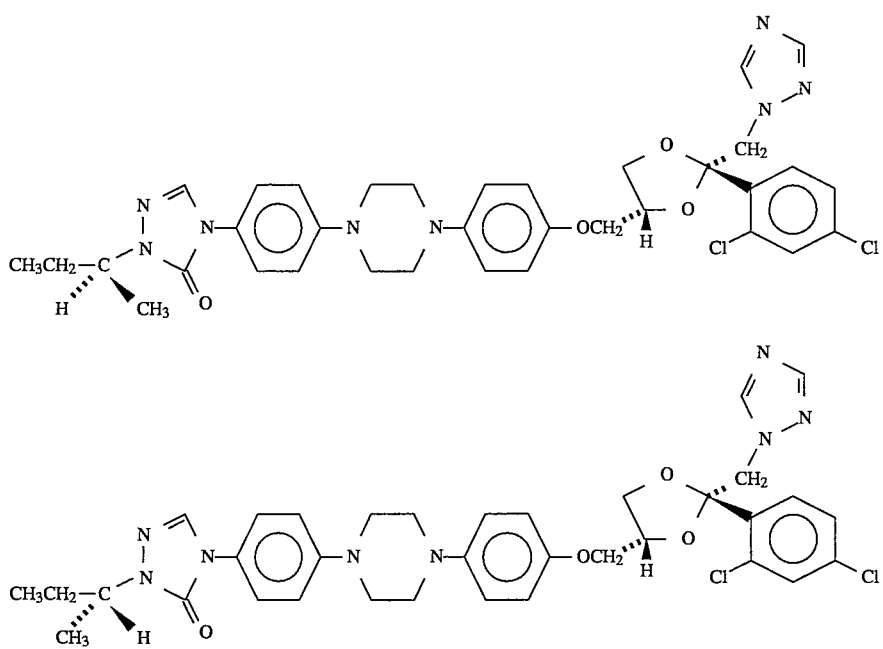

Since the chirality at the sec-butyl carbon is immaterial to the unexpected advantages of the R,S dioxolane configuration disclosed below, the proportion of (R,S,S) to (R,S,R) can range from 100% (R,S,S) to 100% (R,S,R). Furthermore, because (R,S,S) and (R,S,R) are diastereomers, they can be separated on the basis of chemical properties such as solubility and crystallization in achiral media if need be, but there is no need to do so. There are no reports in the literature of the separation of any of the isomers of itraconazole other than cis from trans, i.e. (R,S,S)/(R,S,R)/(S,R,S)/(S,R,R) mixtures from (R,R,R)/(R,R,S)/(S,S,S)/(S,S,R) mixtures. Racemic cis itrazonazole is commercially available as the free base.

Itraconazole is an orally active, broad-spectrum antifungal agent. The compound, a triazole derivative structurally related to miconazole and clotrimazole, impairs the synthesis of ergosterol, which is the principal sterol of fungal cell membranes. This presumably results in an increased permeability and leakage of intracellular content. At high concentration, cellular internal organelles involute, peroxisomes increase, and necrotic changes occur.

Following oral administration, itraconazole is slowly absorbed. Peak plasma levels are attained after 15 days of daily administration, and the pharmacokinetic behavior of itraconazole is nonlinear. The compound is eventually metabolized to several inactive metabolites apparently through hepatic mechanisms and in most subjects no metabolites are excreted in the urine [see Hardin et al., *Antimicro. Agents and Chemotherapy* 32, 1310–1313 (1988)].

The racemic mixture of itraconazole has recently been approved for use as an antifungal agent for blastomycosis and histoplasmosis. The compound is also being investigated for use in aspergillosis, coccidioidomycosis, cryptococcosis, onychomycosis, dermatophyte and candidiasis infections.

Systemic fungal diseases (systemic mycoses) are usually chronic, very slowly developing conditions induced by opportunistic causative fungi which may not normally be pathogenic. However when they enter a host compromised by HIV, ionizing irradiation, corticosteroids, immunosuppressives, etc. or by such conditions as emphysema, bronchiectasis, diabetes mellitus, leukemia, burns and the like, they may become pathogenic. Symptoms in such fungal diseases are generally not intense, and may include fever, chills, anorexia and weight loss, malaise, and depression. Fungal diseases are often confined to typical anatomic distributions, and many involve a primary focus in the lung, with more characteristic manifestations of specific fungal infections when the fungus disseminates from a primary focus. For example, coccidioidomycosis occurs in a primary form as an acute, benign, self-limiting respiratory disease, with progressive disease developing from the primary form as a chronic, often fatal infection of the skin, lymph glands, spleen and liver. Similarly, blastomycosis primarily involves the lungs, and occasionally spreads to the skin. Other infectious diseases such as paracoccidioidomycosis and candidiasis offer a different course, and depending on the etiology may exhibit several forms involving the skin, mucous membranes, lymph nodes, and internal organs. The diagnosis of specific fungal diseases may be made by isolation of the causative fungus from sputum, urine, blood, or the bone marrow, or with prevalent fungus types by evidence of tissue invasion.

Superficial fungal infections are caused by dermatophytes or fungi that involve the outer layers of the skin, hair or nails. The infections may result in a mild inflammation, and cause intermittent remissions and exacerbations of a gradually extending, scaling, raised lesion. Yeast infections including candidiasis, and oral candidiasis (thrush) are usually restricted to the skin, and mucous membranes, and the symptoms vary with the site of infection. Commonly, infections appear as erythematous, often itchy, exudative patches in the axillas, umbilicus, groin, between toes, and on fingerwebs. Oral thrush involves an inflamed tongue, or buccal mucosa and presents as white patches of exudate, while chronic mucocutaneous candidiasis is characterized by red, pustular, crusted, thickened lesions on the forehead or nose.

Many of the "conazole" antifungal agents, including itraconazole, share the same adverse effects. These adverse effects include, but are not limited to, nausea, vomiting, anemia, thrombocytosis, hypersensitivity reactions, hepatotoxicity and some central nervous system toxicity. The racemic mixture of itraconazole has been found to cause nausea and vomiting, anorexia, headache, and dizziness. Hepatotoxicity and hypersensitivity reactions including urticaria and elevations in serum liver enzymes are also associated with the administration of the drug. Hepatotoxicity is a less common but more serious adverse effect. Indeed, the use of oral conazoles as first line antifungals is usually discouraged because of the potentially serious consequences of the low incidence of hepatotoxicity [See, for example, Lavrijsen et al. *Lancet* 340, 251–252 (1992)].

We have found evidence in our own studies in isolated guinea pig hearts that the administration of racemic conazoles may be associated with an increased risk of cardiac arrhythmia. Arrhythmia has not been heretofore reported as a side effect of systemic racemic itraconazole, although a particular subtype of arrhythmia, torsades de pointes, has been reported when racemic itraconazole was administered concurrently with terfenadine. The lack of clinical reports of arrhythmia or QT anomalies may simply be a reflection of the fact that there is to date a relatively small subject population.

Thus it would be particularly desirable to find a compound with the advantages of the racemic mixture of itraconazole which would not have the aforementioned disadvantages.

SUMMARY OF THE INVENTION

It has now been discovered that the optically pure (2R,4S) isomer of itraconazole is an effective agent for treating local and systemic fungal, yeast, and dermatophyte infections that avoids adverse effects associated with the administration of the racemic mixture, including but not limited to hepatotoxicity, arrhythmogenicity, dizziness, elevations in serum liver enzymes, hypersensitivity reactions, urticaria, headache, nausea, and vomiting and abdominal pain. The present invention also includes methods for treating local and systemic fungal, yeast and dermatophyte infections in a human while avoiding the adverse effects that are associated with the racemic mixture of itraconazole, by administering the optically pure (2R,4S) isomer of itraconazole to said human.

DETAILED DESCRIPTION OF THE INVENTION

The present invention encompasses a method of treating local and systemic fungal, yeast and dermatophyte infections in a human, which comprises administering to a human in need of such antiinfective therapy, an amount of (2R,4S) itraconazole, or a pharmaceutically acceptable salt thereof, substantially free of its (2S,4R) stereoisomer, said amount being sufficient to alleviate such infections. The method avoids the concomitant liability of adverse effects associated with the administration of racemic itraconazole by providing an amount of (2R,4S) itraconazole which is insufficient to cause the adverse effects associated with the racemic mixture of itraconazole.

The present invention also encompasses an antiinfective composition for the treatment of a human in need of therapy for systemic or topical fungal, yeast or dermatophyte infection, which comprises an amount of (2R,4S) itraconazole, or a pharmaceutically acceptable salt thereof, substantially free of its (2S,4R) stereoisomer, said amount being sufficient to alleviate said infection. The composition should provide a dose which is insufficient to cause the adverse effects associated with racemic itraconazole.

The available racemic mixture of itraconazole (i.e. a 1:1 mixture of the two enantiomers of the cis diastereomer) possesses antiinfective activity and provides therapy against many fungi, yeasts and dermatophytes; however, this racemic mixture, while offering the expectation of efficacy, causes adverse effects. Utilizing the substantially optically pure or optically pure isomer of itraconazole results in clearer dose related definitions of efficacy, diminished adverse effects, and accordingly, an improved therapeutic index. It is therefore more desirable to administer the (2R,4S) isomer of itraconazole than racemic itraconazole.

The term "adverse effects" includes, but is not limited to, arrhythmogenicity, hepatotoxicity and elevations in serum liver enzymes, hypersensitivity reactions including urticaria, nausea, vomiting, abdominal pain, headache, dizziness and the like.

The term "substantially free of its (2S,4R) stereoisomer" as used herein means that the compositions contain a greater proportion of the (2R,4S) isomer of itraconazole in relation to the (2S,4R) isomer. In a preferred embodiment, the term "substantially free of its (2S,4R) isomer" as used herein means that the composition is at least 90% by weight of (2R,4S) itraconazole and 10% by weight or less of (2S,4R) itraconazole. In a more preferred embodiment the term "substantially free of the (2S,4R) stereoisomer" means that the composition contains at least 99% by weight of (2R,4S) itraconazole, and 1% or less of (2S,4R) itraconazole. In the most preferred embodiment, the term "substantially free of its (2S,4R) stereoisomer" as used herein means that the composition contains greater than 99% by weight of (2R,4S) itraconazole. These percentages are based upon the total amount of itraconazole in the composition. The terms "substantially optically pure (2R,4S) isomer of itraconazole" or "substantially optically pure (2R,4S) itraconazole" and "optically pure (2R,4S) isomer of itraconazole" or "optically pure (2R,4S) itraconazole" are also encompassed by the above-described amounts.

The chemical synthesis of the racemic mixture of itraconazole can be performed by the method described in Heeres, J. et al., *J. Med. Chem,.* 27, 894–900 (1984) and in U.S. Pat. No. 4,267,179. Individual isomers of itraconazole may be obtained by resolution of the racemic mixture of enantiomers using conventional means. The itraconazole may be resolved with an optically active acid such as tartaric acid at any stage in which an asymmetric piperazine is present. Other standard methods of resolution known to those skilled in the art, including but not limited to simple crystallization and chromatographic resolution, can be used. [See for example, Stereochemistry of Carbon Compounds, E. L. Eliel, McGraw Hill (1962); "Tables of Resolving Agents" Wilen and Lochmuller, *J. Chromatography* 113, 283–302 (1975).] The optically pure (2R,4S) isomer can also be prepared from the racemic mixture by enzymatic biocatalytic resolution. See for example, U.S. Pat. Nos. 5,057,427 and 5,077,217, the disclosures of which are incorporated herein by reference. Thus an ester of the 2-(triazolylmethyl)dioxolane- 4-methanol intermediate can be enzymatically resolved. In addition the pure (2R,4S) isomer can be synthesized by a procedure analogous to that described by Rotstein et al. for ketoconazole isomers by stereocontrolled synthesis from optically active dioxolane precursor [see *J. Med. Chem.* 35, 2818–2825 (1992)].

The magnitude of a prophylactic or therapeutic dose of (2R,4S) itraconazole in the acute or chronic management of disease will vary with the severity of the condition to be treated, and the route of administration. The dose, and perhaps the dose frequency, will also vary according to the age, body weight, and response of the individual patient. In general, the total daily dose range, for (2R,4S) itraconazole, for the conditions described herein, is from about 50 mg to about 1200 mg, in single or divided doses. Preferably, a daily dose range should be between about 100 mg to about 800 mg, in single or divided doses, while most preferably, a daily dose range should be between about 200 mg to about 400 mg, in divided doses. In managing the patient, the therapy should be initiated at a lower dose, perhaps about 100 mg to about 200 mg, and increased up to about 400 mg or higher depending on the patient's global response. It is further recommended that children, and patients over 65 years, and those with impaired renal, or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The term "an amount sufficient to alleviate such infections but insufficient to cause said adverse effects" is encompassed by the above-described dosage amounts and dose frequency schedule.

Any suitable route of administration may be employed for providing the patient with an effective dosage of (2R,4S) itraconazole. For example, oral, rectal, parenteral (subcutaneous, intramuscular, intravenous), transdermal, topical and like forms of administration may be employed. Dosage forms include tablets, troches, dispersions, suspensions, solutions, capsules, patches, ointments, creams, shampoos and the like.

The pharmaceutical compositions of the present invention comprise (2R,4S) itraconazole as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like.

The compositions of the present invention include compositions such as suspensions, solutions, elixirs, aerosols, and solid dosage forms. Carriers such as starches, sugars, microcrystalline cellulose, diluents, granulating agents, lubricants, binders, disintegrating agents, and the like, are commonly used in the case of oral solid preparations (such as powders, capsules, and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

A second preferred route of administration is topically, for which creams, ointments, shampoos, and the like are well suited.

In addition to the common dosage forms set out above, the compounds of the present invention may also be administered by controlled release means and/or delivery devices such as those described in U.S. Pat. Nos.: 3,845,770; 3,916,899; 3,536,809; 3,598,123; and 4,008,719; the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 100 mg to about 300 mg of the active ingredient. Most preferably, the tablet, cachet or capsule contains either one of three dosages, about 50 mg, about 100 mg, or about 200 mg of the active ingredient.

For topical application, there are employed as non-sprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

The invention is further defined by reference to the following examples describing in detail the preparation of the compositions of the present invention as well as their utility. It will be apparent to those skilled in the art that many modifications, both to materials and methods may be practiced without departing from the purpose and interest of this invention.

Microbiological and pharmacologic studies can be used to determine the relative potency and the profile of specificity of the optically pure enantiomers, and the racemic mixture of itraconazole as antimycotic agents with a broad spectrum of activity against many fungi, yeast, and dermatophytes.

With respect to antimicrobial activity of the aforementioned compounds, selected experiments are illustrated to profile useful antimicrobial activity, and not to limit this invention in any way, including the scope of susceptible microorganisms. Antifungal conazoles may be evaluated in vitro at several concentrations (in μg/ml) against a number of fungi and bacteria. [see Van Cutsem *Chemotherapy* 38 *Suppl* 1, 3-11 (1992) and Van Cutsem et al. *Rev. Infec. Dis.* 9 *Suppl* 1, S15–S32 (1987)]. The fungistatic assay is carried out in Sabouraud's liquid (1 g of neopeptone Difco and 2 g of glucose Difco per 100 mL of distilled water) in 16×160 mm test tubes, each containing 4.5 mL of liquid medium which has been autoclaved at 120° for 5 min. The compounds to be tested are dissolved in 50% alcohol at initial concentration of 20 mg/mL. The solutions are subsequently diluted with sterile distilled water to give a concentration of 10 mg/mL. Successive decimal dilutions are made in distilled water. To tubes containing 4.5 mL of Sabouraud's liquid medium 0.5 mL of the solution of the drug is added, thereby obtaining concentrations of 1000, 500, 100, 10, and 1 μg/mL of medium. Control tubes are prepared by adding 0.5 mL of distilled water to 4.5 of mL medium, alcohol being added to give concentrations identical with the tubes containing 1000 and 500 μg of the drug. The filamentous fungi are incubated in Sabouraud's agar at 25° for 2–3 weeks. A block of 2× 2×2 mm is then inoculated into the medium. All cultures are made in duplicate and are incubated at 25° for 14 days. Itraconazole antifungal activity is enhanced in vitro in Sabouraud broth containing 10% inactivated bovine serum, and depends on the test medium used. Complete or marked inhibition of growth in Sabouraud broth after 14 days of incubation may be observed with *Microsporum canis, Trichophyton mentagrophytes, Candida albicans, Sporothrix schenckii, Paracoccidioides brasiliensis, Blastomyces dermatitides*, Histoplasma spp., Aspergillus spp. and other fungi and bacteria. Concentration/response curves may be compared for itraconazole, its isomers, and such standard agents as miconazole, as regards scope, and potency.

In vivo activity of itraconazole and the optically pure enantiomers may be compared against experimental cutaneous candidosis in guinea pigs, and vaginal candidosis in rats. The in vivo activity of the compounds in vaginal candidosis is evaluated by inducing vaginal infection with *C. albicans* in ovariectomized and hysterectomized Wistar rats (100 g) which are treated weekly with 100 μg of estradiol undecanoate in sesame oil, subcutaneously. Animals in pseudooestrus are infected intravaginally with a fixed concentration of *C. albicans* in saline. Control of infection or cure is estimated by taking vaginal smears at fixed days after infection. Drugs to be evaluated, and compared on a mg/kg basis, may be given prophylactically, or therapeutically and their efficacy judged by comparison the ratio of negative animals to the total number in each drug group. In similar studies, the activity against cutaneous candidosis in guinea pigs [(Van Cutsem et al. *Chemotherapy* 17, 392, (1972)] provides the basis of comparison between the racemate and enantiomers of itraconazole.

The potential for promoting arrhythmia is evaluated by examining the effects of the optically pure isomers of itraconazole on cardiac action potential and contractility in human and canine hearts.

Torsades de pointes is a well known side effect of antiarrhythmic drugs, such as quinidine, sotalol and acetylprocainamide, which cause a prolongation of cardiac repolarization. All of these drugs have in common the ability to block a cellular potassium channel called the delayed rectifier ($I_k$), and it is generally assumed that this is mechanistically linked to their ability to induce the syndrome of torsades de pointes. [See Zehender et al. *Cardiovascular Drugs Ther.*, 515–530 (1991).]

Increases in QT duration and action potential duration in isolated guinea pig hearts can be used to indicate an arrhythmogenic effect. Hearts are perfused with an oxygenated Tyrode's solution, containing 0.0; 1.0; 5.0 or 10.0 μM of racemic itraconazole. QT duration and action potential duration (APD) are measured from cardiac electrodes. In separate experiments, the hearts are divided into 3 subgroups receiving either the (2R,4S) enantiomer, (2S,4R) enantiomer, or racemate to determine the respective effects on QT duration and APD.

To observe the effects in vivo, mongrel dogs of either sex weighing 5–20 kg are anesthetized and instrumented by standard techniques for blood pressure and EKG. A solid state transducer for dP/dT is placed in the left cardiac ventricle, and an epicardial electrode is put into place. The test compound is infused at progressively higher doses, beginning at 1 μg/kg/min for 15 minutes and increased incrementally until a cardiovascular collapse ensues. Parameters measured are: blood pressure, heart rate, dP/dT, and the QT-interval. Measurements of hemodynamics and electrical activity are made in response to the (2R,4S) enantiomer, (2S,4R) enantiomer and racemate.

The potential for promoting hepatotoxicity is assessed in vitro in human hepatic microsomes and human lymphocytes. Hepatic microsomes are prepared from human liver. Tissue is thawed and then homogenized in 0.15M KCl in a Polytron homogenizer. The homogenate is centrifuged and the pellet is resuspended and homogenized in 0.15M KCl. Aliquots are frozen and stored at −70° C. Human lymphocytes are aseptically isolated from fresh, heparinized human blood. Blood is diluted with Eagle's minimal essential medium and layered on Ficoll-Paque. The samples are centrifuged, and lymphocytes are then removed from the aqueous-Ficoll interface and suspended in medium (15 Mm HEPES, pH, 7.4). The cells are then centrifuged, washed once in the HEPES medium, and resuspended.

Cytotoxicity is assessed by the conversion of 3-( 4,5 dimethylthiazol-2-yl)-2,5-diphenyltetrazolium bromide (MTT) to a purple formazan. The conversion of MTT to dye is done in multiwell plates. After preparation, hepatic microsomes or lymphocytes are incubated alone or with the test compound in a concentration range from 1 to 400 μM at 37° C. in a humidified incubator. After incubation, the microsomes/cells are washed with 5% albumin in HEPES-buffered medium and resuspended. The microsomes/cells are then incubated at 37° C. in a humidified incubator. After the incubation, 125 μg of MTT is added to each well. The plates are incubated at 37° C. and centrifuged. After centrifugation, 100 μL of isopropanol is added and, after incubation, the optical density is determined using an automated plate-reader.

EXAMPLE 1
ORAL FORMULATION
Capsules:

| Formula | Quantity per capsule in mg | | |
|---|---|---|---|
| | A | B | C |
| (2R,4S) Itraconazole | 50 | 100 | 200 |
| Lactose | 380 | 330 | 230 |
| Cornstarch | 65 | 65 | 65 |
| Magnesium Stearate | 5 | 5 | 5 |
| Compression Weight | 500 | 500 | 500 |

The active ingredient, (2R,4S) itraconazole, is sieved and blended with the excipients. The mixture is filled into suitably sized two-piece hard gelatin capsules using suitable machinery. Other doses may be prepared by altering the fill weight and if necessary, changing the capsule size to suit.

EXAMPLE 2
ORAL FORMULATION
Tablets:

| Formula | Quantity per tablet in mg | | |
|---|---|---|---|
|  | A | B | C |
| (2R,4S) Itraconazole | 50 | 100 | 200 |
| Lactose | 109 | 309 | 209 |
| Cornstarch | 30 | 30 | 30 |
| Water | 300 mL | 300 mL | 300 mL |
| (per thousand Tablets)* | | | |
| Cornstarch | 60 | 60 | 60 |
| Magnesium Stearate | 1 | 1 | 1 |
| Compression Weight | 250 | 500 | 500 |

*The water evaporates during manufacture

The active ingredient is blended with the lactose until a uniform blend is formed. The smaller quantity of cornstarch is blended with the water to form the resulting cornstarch paste. This is then mixed with the uniform blend until a uniform wet mass is formed and the remaining cornstarch is added and mixed until uniform granules are obtained. The granules are screened through a suitable milling machine using a ¼" stainless steel screen. The milled granules are dried in a suitable drying oven and milled through a suitable milling machine again. The magnesium stearate is then blended and the resulting mixture is compressed into tablets of desired shape, thickness, hardness and disintegration.

What is claimed is:

1. A method for treating local and systemic fungal, yeast and dermatophyte infections in a human which comprises administering to a human, in need of antiinfective therapy, an amount of (2R,4S) itraconazole, or a pharmaceutically acceptable salt thereof, substantially free of its (2S,4R) stereoisomer, said amount being sufficient to alleviate said infections.

2. A method for treating local and systemic fungal, yeast and dermatophyte infections in a human while avoiding the concomitant liability of adverse effects associated with racemic itraconazole, which comprises administering to a human, in need of antiinfective therapy, an amount of (2R,4S) itraconazole, or a pharmaceutically acceptable salt thereof, substantially free of its (2S,4R) stereoisomer, said amount being sufficient to alleviate said infection but insufficient to cause said adverse effects.

3. The method of claim 2 wherein (2R,4S) itraconazole is administered by intravenous infusion, transdermal delivery, or orally as a tablet or a capsule.

4. The method of claim 3 wherein the amount of (2R,4S) itraconazole or a pharmaceutically acceptable salt thereof administered is from about 50 mg to about 1200 mg per day.

5. The method of claim 4 wherein the amount administered is from about 100 mg to about 800 mg per day.

6. The method of claim 5 wherein the amount administered is from about 200 mg to about 400 mg per day.

7. The method of claim 1 wherein the amount of (2R,4S) itraconazole or a pharmaceutically acceptable salt thereof is greater than approximately 90% by weight of the total weight of itraconazole.

8. The method of claim 1 wherein the amount of said (2R,4S) itraconazole or a pharmaceutically acceptable salt thereof, substantially free of its (2S,4R) stereoisomer, is administered together with a pharmaceutically acceptable carrier.

9. An anti-infective composition for the treatment of a human in need of therapy for a systemic or topical fungal, yeast or dermatophyte infection which comprises a pharmaceutically acceptable carrier and a therapeutically effective amount of (2R,4S) itraconazole or a pharmaceutically acceptable salt thereof, substantially free of its (2S,4R) stereoisomer.

10. The composition according to claim 9 wherein the amount of (2R,4S) itraconazole is from about 50 mg to about 1200 mg.

11. The composition according to claim 10 wherein the amount of (2R,4S) itraconazole is from about 100 mg to about 1000 mg.

12. The composition according to claim 9 wherein said composition is adapted for oral administration.

13. The composition according to claim 9 adapted for parenteral delivery.

14. The composition according to claim 13 adapted for intramuscular delivery.

15. The composition according to claim 9 adapted for topical delivery.

* * * * *